US006303627B1

(12) United States Patent
Koch et al.

(10) Patent No.: US 6,303,627 B1
(45) Date of Patent: Oct. 16, 2001

(54) INHIBITORS OF SEROTONIN REUPTAKE

(75) Inventors: Daniel James Koch; Vincent Patrick Rocco, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/325,302

(22) Filed: Jun. 3, 1999

Related U.S. Application Data

(60) Provisional application No. 60/090,070, filed on Jun. 19, 1998.

(51) Int. Cl.[7] .................. A61K 31/44; A61K 31/445; C07D 401/00; C07D 215/20; C07D 215/16
(52) U.S. Cl. .................. 514/307; 514/309; 514/314; 514/319; 514/320; 514/323; 546/153; 546/156; 546/169; 546/178; 546/180; 546/181; 546/197; 546/198; 546/199; 546/201
(58) Field of Search .................. 546/197, 198, 546/199, 201, 153, 156, 169, 178, 180, 181; 514/319, 320, 323, 307, 309, 314

(56) References Cited

U.S. PATENT DOCUMENTS

| | | | |
|---|---|---|---|
| 3,890,441 | 6/1975 | Schenker et al. | 424/267 |
| 4,246,268 | 1/1981 | Carr | 546/346 |
| 4,284,638 | 8/1981 | Waldmeier et al. | 546/269 |
| 4,600,719 | 7/1986 | Schenker et al. | 514/320 |
| 4,670,447 | 6/1987 | Strupczewski | 514/322 |
| 5,196,425 | 3/1993 | Vandenberk et al. | 514/258 |
| 5,292,761 | 3/1994 | Lavielle et al. | 514/255 |
| 5,472,966 | 12/1995 | Sloan et al. | 514/357 |

FOREIGN PATENT DOCUMENTS

| | | |
|---|---|---|
| 613452 | 9/1979 | (CH) . |
| 0 343 830 | 11/1989 | (EP) . |
| 0 648 767 | 4/1995 | (EP) . |
| 0 812 826 | 12/1997 | (EP) . |
| WO 95 33721 | 12/1995 | (WO) . |
| WO 98 51668 | 11/1998 | (WO) . |

OTHER PUBLICATIONS

Database CAS: Rhone–Poulenc, (France), 115:232233 Gueremy, et al. Preparation and formulation of 2–4–indolyl– methyl piperidinoethylnaptho– isothiazole–1,1,–dioxides and analogs as serotonin reuptake inhibitors (1992).

Database CAS: Unversity California (San Francisco CA. USA.), 116:101623 TAN, et al. Differences in substrate specificities of monamine oxidase A from human liver and placenta (1991).

Glennon R. A. et al.: "5–HT1D Receptors: A Serotonin Receptor Population for the 1990S" Drug News and Perspectives. vol. 6, No. 6, Jul. 1, 1993 pp. 390–405.

Macor, J. E. et al.: "3–(1,2,5,6–Tetrahydropyrid–4–YL) Pyrrolo [3,2–B] Pyrid–5–One: A Potent and Selective Serotonin (5–HT1B) Agonist and Rotationally Restricted Phneolic Analogue of 5–Methoxy–3–(1,2,5, 6–Tetrahydro–Pyrid–4–YL) Indole" J. Med. Chem, vol. 33, No. 8, 1990, pp. 2087–2093.

Nelson, D.L.: "Structure Activity Relationships at 5–HT Receptors: Binding Profiles and Intrinsic Activity" Pharmacology Biochemistry and Behavior, vol. 40, Jan. 1, 1991, pp. 1041–1051.

Efange, S.M.N., et al.: "Flexible N–Methyl–4–Phenyl–1,2, 3,6–Tetrahydropyrrdine Analogues: Synthesis Monamine Oxidase Catalyzed Bioactivation" J. Med. Chem., vol. 33, No. 12, 1990, pp. 3133–3138.

Plaquevent, J.C., et al.: "Reduction Regiospecifique des Bipyridines" Tetrahedron Lett. Col. 34, No. 33, 1993, pp. 5287–5288.

Saari, W.S.: "Adrenoceptor and Tetrabenazine Antagonism Activities of Som Pyridinyltetrahydropyridines" J. Med. Chem, vol. 27, No. 9, 1984, pp. 1182–1185.

Franot, C., et al.: "Chemical Model Studies on the Monamine Oxidase–B Catalyzed Oxidation of 4–Substituted 1–Cyclo–Propyl–1,2,3,6–Tetrahydropyridines" Biorg. Med. Chem., vol. 6, 1998, pp. 283–291.

Carelli, V., et al.: "Su Alcuni Derivati Gamma–Piridin–E Gamma–Chinolin–Piperidinici" Ann. Chim., vol. 49, 1959, pp. 709–719.

Primary Examiner—Alan L. Rotman
Assistant Examiner—Raymond Covington
(74) Attorney, Agent, or Firm—R. Craig Tucker; Robert D. Titus

(57) ABSTRACT

This invention provides compounds and a method for the inhibition of serotonin reuptake in mammals.

7 Claims, No Drawings

INHIBITORS OF SEROTONIN REUPTAKE

PRIORITY INFORMATION

This application claims the benefit of U.S. Provisional Application No. 60/090,070, filed Jun. 19, 1998.

BACKGROUND OF THE INVENTION

During the past two decades, the relationship between neuronal monoamines in the brain and a variety of diseases and conditions has been appreciated and investigated. The discovery of selective monoamine reuptake inhibitors has provided the medical community with exciting new tools with the potential for treatment of several physiological and psychological disorders. Reuptake inhibitors increase the levels of endogenous monoamines by inhibiting the neuronal mechanism for recovering the monoamine from the synapse without interfering with the neuronal receptors. If the reuptake inhibitor is selective for a particular monoamine, undesirable side-effects from the therapy can be reduced.

Fluoxetine, a selective inhibitor of serotonin reuptake, has gained wide acceptance as a therapy for the treatment of depression and eating disorders, and is under active investigation for the treatment of other disorders. Similarly, tomoxetine hydrochloride [(-)-N-methyl-3-(2-methylphenoxy)propanamine hydrochloride] is a selective inhibitor of norepinephrine uptake being investigated clinically for the treatment of urinary incontinence. These compounds are among many taught in U.S. Pat. Nos. 4,018,895, 4,194,009, 4,314,081 and 5,026,707 as being potent inhibitors of the uptake of various physiologically active monoamines, including serotonin, norepinephrine and dopamine. The present invention provides 4-arylpiperidines useful for the inhibition of serotonin reuptake.

SUMMARY OF THE INVENTION

The present invention provides 4-arylpiperidines of formula I:

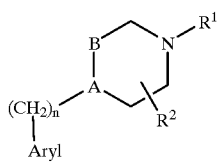

where

A—B is —C=CH— or —CHCH$_2$—;

n is 0 or 1;

R$^1$ is H or C$_1$–C$_4$ alkyl;

R$^2$ is H, or C$_1$–C$_6$ alkyl; and

Aryl is naphthyl or heteroaryl, each optionally monosubstituted with a substitutent selected from the group consisting of halo, hydroxy, C$_1$–C$_4$ alkyl, C$_1$–C$_4$ alkoxy, cyano, nitro, carboxamido, and trifluoromethyl; or pharmaceutically acceptable salts or hydrates thereof.

This invention also provides a pharmaceutical formulation which comprises, in association with pharmaceutically acceptable carriers, diluents or excipients, a compound of Formula I.

This invention further comprises a method for the inhibition of serotonin reuptake comprising administering to a mammal in need of such treatment an effective amount of a compound of Formula I.

DETAILED DESCRIPTION

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "alkoxy" includes methoxy, ethoxy, propoxy, isopropoxy, butoxy and the like. The term "halogen" includes fluoro, chloro, bromo and iodo.

The term "naphthyl" is taken to mean naphth-1-yl or naphth-2-yl.

The term "heteroaryl" is taken to mean benzofur-2-yl, benzofur-3-yl, indazol-3-yl, benzimidazol-2-yl, benzothiazol-2-yl, benzoxazol-2-yl, benzoisothiazol-3-yl, benzoisoxazol-3-yl, quinolin-2-yl, quinolin-3-yl, quinolin-4-yl, isoquinolin-1-yl, isoquinolin-3-yl, and isoquinolin-4-yl.

While all of the compounds of Formula I are useful for the inhibition of serotonin reuptake, certain classes of the compounds are preferred. The following paragraphs describe such preferred classes.

a) A—B is —C=CH—;
b) A—B is —CH—CH$_2$—;
c) R$^1$ is hydrogen;
d) R$^1$ is methyl;
e) Aryl is naphthyl;
f) Aryl is heteroaryl;
g) Aryl is selected from benzothiazol-2-yl, benzofur-2-yl, and quinolin-2-yl;
h) Aryl is monosubstituted with halogen;
i) Aryl is monosubstituted with chloro;
j) Aryl is benzothiazol-2-yl;
k) Aryl benzofur-2-yl monosubstituted at the 6-position;
l) R$^2$ is hydrogen;
m) R$^2$ is methyl;
n) A—B is —CHCH$_2$—, n is 0, R$^2$ is methyl at the 2-position of the piperidine ring, and the compound exists as the trans-isomer;
o) n is 0;
p) The compound is a salt;
q) The compound is a free base.

It will be understood that the above classes may be combined to form additional preferred classes.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

Certain compounds of the invention where $R^2$ is methyl or ethyl are chiral. As such, these compounds may exist as single members of specific optical isomer pairs (a)–(f), as mixtures of these optical isomer pairs, or as racemic mixtures of these optical isomer pairs. The skilled artisan will also appreciate that the isomer pairs (a)–(d) exist as diastereomers, since the alkyl moiety creates an element of asymmetry at the 4-position of the piperidine nucleus. All of these diastereomers and enantiomers are contemplated by the present invention.

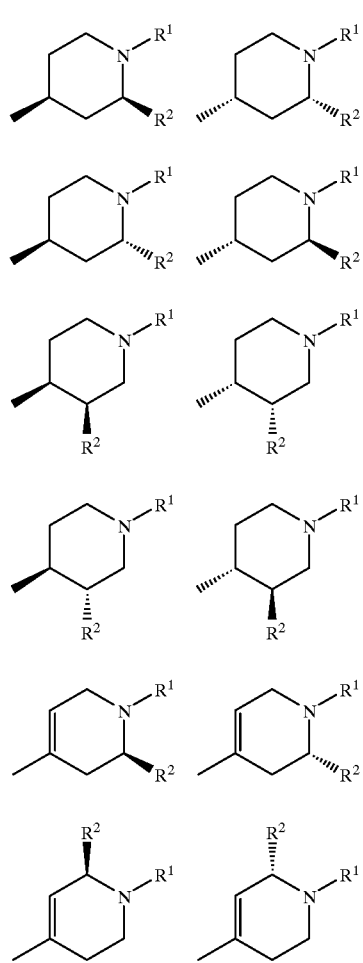

While all racemates, diastereomers, single enantiomers, and mixtures of enantiomers are useful serotonin reuptake inhibitors, it is preferred that the compound be a single enantiomer or diastereomer.

It is especially preferred that the compound contains a moiety of formula (b).

The skilled artisan will appreciate that the pure isomers may be prepared from chiral starting materials, or by fractional crystallization using chiral acids. Additionally, compounds of the invention where $R^1$ is H may be used as intermediates by introducing a chiral auxiliary, separating the diastereomers by fractional crystallization or chromatography, and then cleaving the chiral auxiliary. $R^1$ substituents other than H may then be reintroduced, as desired, by reductive alkylation or alkylation with an appropriate reagent.

The following group is illustrative of the compounds of the present invention:

(+)-trans-2-methyl-4-(benzofur-3-yl)piperidine sulfate;

4-(4-bromobenzofur-2-yl)-1,2,3,6-tetrahydropyridine phosphate;

4-(5-fluorobenzofur-3-yl)piperidine hydrochloride;

4-(6-iodobenzofur-2-yl)piperidine;

(−)-cis-1,2-dimethyl-4-(7-hydroxybenzofur-3-yl) piperidine hydrobromide monohydrate;

4-(4-methylbenzofur-2-ylmethyl)piperidine acetate;

4-(5-isopropylbenzofur-3-yl)piperidine;

trans-1-methyl-3-ethyl-4-(6-isobutylbenzofur-2-yl) piperidine acrylate;

4-(7-ethoxybenzofur-3-yl)piperidine succinate;

4-(4-tert-butoxybenzofur-2-yl)piperidine;

1-isopropyl-4-(5-cyanobenzofur-3-yl)-1,2,3,6-tetrahydropyridine dinitrobenzoate;

4-(6-nitrobenzofur-2-yl)piperidine;

1-butyl-4-(6-carboxamidobenzofur-3-yl)piperidine;

4-(7-trifluoromethybenzofur-2-yl)piperidine citrate;

(+)-trans-2-methyl-4-(indazol-3-yl)piperidine sulfate;

4-(4-bromoindazol-yl)-1,2,3,6-tetrahydropyridine phosphate;

4-(5-fluoroindazol-3-yl)piperidine hydrochloride;

4-(6-iodoindazol-3-ylmethyl)piperidine;

(−)-cis-1,2-dimethyl-4-(7-hydroxyindazol-3-yl) piperidine hydrobromide monohydrate;

4-(4-methylindazol-3-yl)piperidine acetate;

4-(5-isopropylindazol-3-yl)piperidine;

trans-1-methyl-3-ethyl-4-(6-isobutylindazol-3-yl) piperidine acrylate;

4-(7-ethoxyindazol-3-yl)piperidine succinate;

4-(4-tert-butoxyindazol-3-yl)piperidine;

1-isopropyl-4-(5-cyanoindazol-3-yl)-1,2,3,6-tetrahydropyridine dinitrobenzoate;

4-(6-nitroindazol-3-yl)piperidine;

1-butyl-4-(6-carboxamidoindazol-3-yl)piperidine;

4-(7-trifluoromethyindazol-3-yl)piperidine citrate;

(+)-trans-2-methyl-4-(benzimidazol-2-yl)piperidine;

4-(4-bromobenzimidazol-2-yl)-1,2,3,6-tetrahydropyridine;

4-(5-fluorobenzimidazol-2-ylmethyl)piperidine tartarate;

4-(6-iodobenzimidazol-2-yl)piperidine;

(−)-cis-1,2-dimethyl-4-(7-hydroxybenzimidazol-2-yl) piperidine;

4-(4-methylbenzimidazol-2-yl)piperidine;

4-(5-isopropylbenzimidazol-2-yl)piperidine mandelate;

trans-1-methyl-3-ethyl-4-(6-isobutylbenzimidazol-2-yl) piperidine;

4-(7-ethoxybenzimidazol-2-yl)piperidine;

4-(4-tert-butoxybenzimidazol-2-yl)piperidine;
1-isopropyl-4-(5-cyanobenzimidazol-2-yl)-1,2,3,6-tetrahydropyridine;
4-(6-nitrobenzimidazol-2-yl)piperidine;
1-butyl-4-(6-carboxamidobenzimidazol-2-yl)piperidine;
4-(7-trifluoromethybenzimidazol-2-yl)piperidine;
(+)-trans-2-methyl-4-(benzothiazol-2-yl)piperidine;
4-(4-bromobenzothiazol-2-ylmethyl)-1,2,3,6-tetrahydropyridine;
4-(5-fluorobenzothiazol-2-yl)piperidine;
4-(6-iodobenzothiazol-2-yl)piperidine;
(−)-cis-1,2-dimethyl-4-(7-hydroxybenzothiazol-2-yl)piperidine;
4-(4-methylbenzothiazol-2-yl)piperidine;
4-(5-isopropylbenzothiazol-2-yl)piperidine;
trans-1-methyl-3-ethyl-4-(6-isobutylbenzothiazol-2-yl)piperidine;
4-(7-ethoxybenzothiazol-2-yl)piperidine;
4-(4-tert-butoxybenzothiazol-2-yl)piperidine;
1-isopropyl-4-(5-cyanobenzothiazol-2-yl)-1,2,3,6-tetrahydropyridine;
4-(6-nitrobenzothiazol-2-yl)piperidine;
1-butyl-4-(6-carboxamidobenzothiazol-2-yl)piperidine;
4-(7-trifluoromethybenzothiazol-2-yl)piperidine;
(+)-tran-2-methyl-4-(benzoxazol-2-yl)piperidine;
4-(4-bromobenzoxazol-2-yl)-1,2,3,6-tetrahydropyridine;
4-(5-fluorobenzoxazol-2-yl)piperidine;
4-(6-iodobenzoxazol-2-yl)piperidine;
(−)-cis-1,2-dimethyl-4-(7-hydroxybenzoxazol-2-yl) piperidine;
4-(4-methylbenzoxazol-2-yl)piperidine;
4-(5-isopropylbenzoxazol-2-yl)piperidine;
trans-1-methyl-3-ethyl-4-(6-isobutylbenzoxazol-2-yl)piperidine;
4-(7-ethoxybenzoxazol-2-yl)piperidine;
4-(4-tert-butoxybenzoxazol-2-ylmethyl)piperidine;
1-isopropyl-4-(5-cyanobenzoxazol-2-yl)-1,2,3,6-tetrahydropyridine;
4-(6-nitrobenzoxazol-2-yl)piperidine;
1-butyl-4-(6-carboxamidobenzoxazol-2-yl)piperidine;
4-(7-trifluoromethybenzoxazol-2-yl)piperidine;
(+)-trans-2-methyl-4-(benzoisothiazol-3-yl)piperidine;
4-(4-bromobenzoisothiazol-3-yl)-1,2,3,6-tetrahydropyridine;
4-(5-fluorobenzoisothiazol-3-yl)piperidine;
4-(6-iodobenzoisothiazol-3-yl)piperidine;
(−)-cis-1,2-dimethyl-4-(7-hydroxybenzoisothiazol-3-yl)piperidine;
4-(4-methylbenzoisothiazol-3-yl)piperidine;
4-(5-isopropylbenzoisothiazol-3-yl)piperidine;
trans-1-methyl-3-ethyl-4-(6-isobutylbenzoisothiazol-3-yl)piperidine;
4-(7-ethoxybenzoisothiazol-3-yl)piperidine;
4-(4-tert-butoxybenzoisothiazol-3-yl)piperidine;
1-isopropyl-4-(5-cyanobenzoisothiazol-3-yl)-1,2,3,6-tetrahydropyridine;
4-(6-nitrobenzoisothiazol-3-yl)piperidine;
1-butyl-4-(6-carboxamidobenzoisothiazol-3-yl)piperidine;
4-(7-trifluoromethybenzoisothiazol-3-yl)piperidine;
(+)-trans-2-methyl-4-(benzoisoxazol-3-yl)piperidine;
4-(4-bromobenzoisoxazol-3-yl)-1,2,3,6-tetrahydropyridine;
4-(5-fluorobenzoisoxazol-3-yl)piperidine;
4-(6-iodobenzoisoxazol-3-yl)piperidine;
(−) -cis-1,2-dimethyl-4-(7-hydroxybenzoisoxazol-3-yl)piperidine;
4-(4-methylbenzoisoxazol-3-yl)piperidine;
4-(5-isopropylbenzoisoxazol-3-yl)piperidine;
trans-1-methyl-3-ethyl-4-(6-isobutylbenzoisoxazol-3-yl)piperidine;
4-(7-ethoxybenzoisoxazol-3-yl)piperidine;
4-(4-tert-butoxybenzoisoxazol-3-yl)piperidine;
1-isopropyl-4-(5-cyanobenzoisoxazol-3-yl)-1,2,3,6-tetrahydropyridine;
4-(6-nitrobenzoisoxazol-3-yl)piperidine;
1-butyl-4-(6-carboxamidobenzoisoxazol-3-yl)piperidine;
4-(7-trifluoromethybenzoisoxazol-3-yl)piperidine;
(+)-trans-2-methyl-4-(quinolin-2-yl)piperidine;
4-(5-bromoquinolin-3-yl)-1,2,3,6-tetrahydropyridine;
4-(6-fluoroquinolin-4-yl)piperidine;
4-(7-iodoquinolin-2-yl)piperidine;
(−)-cis-1,2-dimethyl-4-(8-hydroxyquinolin-3-yl)piperidine;
4-(5-methylquinolin-4-ylmethyl)piperidine;
4-(6-isopropylquinolin-2-yl)piperidine;
trans-1-methyl-3-ethyl-4-(7-isobutylquinolin-3-yl)piperidine;
4-(8-ethoxyquinolin-4-yl)piperidine;
4-(5-tert-butoxyquinolin-2-yl)piperidine;
1-isopropyl-4-(6-cyanoquinolin-2-yl)-1,2,3,6-tetrahydropyridine;
4-(7-nitroquinolin-2-yl)piperidine;
1-butyl-4-(6-carboxamidoquinolin-2-yl)piperidine;
4-(8-trifluoromethyquinolin-2-yl)piperidine;
(+)-trans-2-methyl-4-(isoquinolin-3-yl)piperidine;
4-(5-bromoisoquinolin-1-yl)-1,2,3,6-tetrahydropyridine;
4-(6-fluoroisoquinolin-4-yl)piperidine;
4-(7-iodoisoquinolin-3-yl)piperidine;
(−)-cis-1,2-dimethyl-4-(8-hydroxyisoquinolin-1-ylmethyl)piperidine;
4-(5-methylisoquinolin-4-yl)piperidine;
4-(6-isopropylisoquinolin-3-yl)piperidine;
trans-1-methyl-3-ethyl-4-(7-isobutylisoquinolin-1-yl)piperidine;
4-(8-ethoxyisoquinolin-4-yl)piperidine;
4-(5-tert-butoxyisoquinolin-3-yl)piperidine;
1-isopropyl-4-(6-cyanoisoquinolin-3-yl)-1,2,3,6-tetrahydropyridine;
4-(7-nitroisoquinolin-3-yl)piperidine;
1-butyl-4-(6-carboxamidoisoquinolin-3-yl)piperidine;
4-(8-trifluoromethyisoquinolin-3-yl)piperidine.

Certain compounds of the present invention may be prepared from appropriate arylhalides by methods well known to the skilled artisan. The necessary arylhalides are either commercially available or may be prepared by methods commonly employed by one of ordinary skill in the art. The preparation of the compounds of the present invention is illustrated in Synthetic Scheme I, where Aryl* is benzofur-2-yl, benzofur-3-yl, naphth-1-yl, naphth-2-yl, quinolin- 3-yl, quinolin-4-yl, or isoquinolin-4-yl; halide is chloro, bromo or iodo; $R^{1*}$ is $C_1-C_4$ alkyl or an appropriate nitrogen protecting group; and $R^1$ and $R^2$ are as previously defined. Nitrogen protecting groups useful for these reactions are well known to the skilled artisan (Greene, *Protective Groups in Organic Synthesis*, Second Edition, Wiley Interscience, New York (1991)). Preferred protecting groups are the $C_1-C_4$ alkoxycarbonyl groups, such as ethoxycarbonyl and tert-butoxycarbonyl, the phenoxycarbonyl group, and the benzyl group.

Synthetic Scheme I

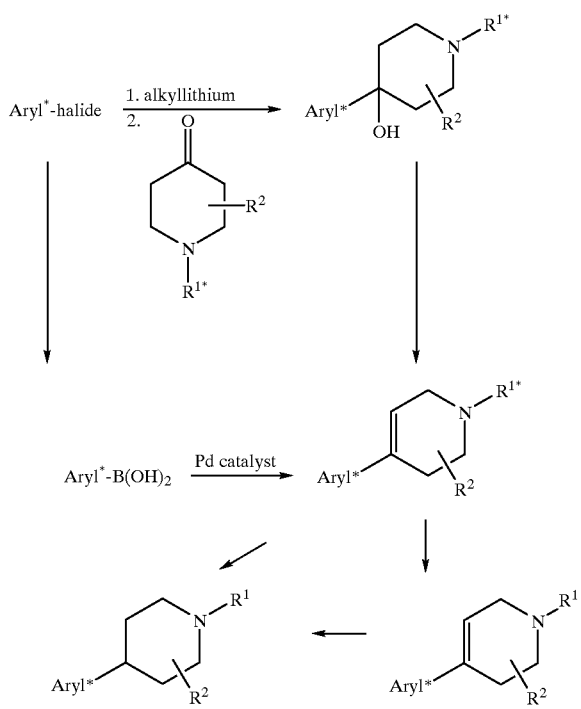

An appropriate aryihalide is reacted with an alkyllithium, typically n-butyllithium or tert-butyllithium, in an appropriate solvent, typically tetrahydrofuran or diethyl ether, to generate the corresponding aryllithium. This aryllithium is then reacted directly with an appropriately substituted 4-piperidone to prepare the corresponding 4-hydroxy-4-arylpiperidine. The requisite 4-piperidones are either commercially available or may be prepared by methods well known to the skilled artisan.

This tertiary alcohol may then be dehydrated to prepare the desired 4-aryl-1,2,3,6-tetrahydropyridine by treatment with an acid in an appropriate solvent. The solvent must be capable of solvating the tertiary alcohol as well as inert to the reaction conditions. Preferred solvents are toluene and dichloromethane. The acid may be soluble in the reaction mixture or may be an acidic resin which is insoluble in the reaction mixture. Trifluoroacetic acid is a preferred soluble acid and AMBERLYST 15™ (Aldrich Chemical Company, P.O. Box 2060, Milwaukee, Wis. 53201, USA) is a preferred acidic resin. The dehydration reactions may be run at from about ambient temperature to the reflux temperature of the solvent.

Once the dehydration is complete, the reaction mixture is concentrated under reduced pressure. In those cases where an acidic resin is used, it is more convenient to remove the resin by filtration prior to concentration of the reaction mixture under reduced pressure. The residue is then dissolved in a water immiscible solvent, such as dichloromethane, and the organic solution is washed with an aqueous base such as sodium bicarbonate solution. The remaining organic phase is dried and then concentrated under reduced pressure. The residue may be used directly in other reactions, converted to an appropriate salt, crystallized or purified by chromatography as desired.

Alternatively, the aryllithiums prepared supra may be treated with a trialkylborate, typically triisopropylborate, to provide, after hydrolysis, the corresponding boric acid. The boric acid derivative may be coupled with an appropriate triflate in the presence of a palladium catalyst, typically tetrakis [triphenylphosphine]palladium(0), to provide the requisite 4-aryl-1,2,3,6-tetrahydro-4-pyridines. The requisite triflates are prepared from the enolates of the corresponding 4-piperidones by treatment with N-phenyltrifluoromethanesulfonimide under conditions well known in the art.

The 4-aryl-1,2,3,6-tetrahydro-4-pyridines prepared by either of these routes may be used to prepare other tetrahydropyridines of the invention, or may be hydrogenated over a precious metal catalyst, such as palladium on carbon or platinum oxide, to give the corresponding 4-arylpiperidines. When the aryl group is substituted with bromo or iodo, a hydrogenation catalyst such as sulfided platinum on carbon, platinum oxide, or a mixed catalyst system of sulfided platinum on carbon with platinum oxide is used to prevent hydrogenolysis of the bromo substituent during reduction of the tetrahydropyridinyl double bond. The hydrogenation solvent may consist of a lower alkanol, such as methanol or ethanol, or a mixed solvent system of ethanol and trifluoroethanol. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The 4-arylpiperidines prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

As an alternative to hydrogenation, the 4-aryl-1,2,3,6-tetrahydropyridines may be reduced by treatment with triethylsilane if desired. The 4-aryl-1,2,3,6-tetrahydropyridine is dissolved in trifluoroacetic acid to which is added an excess, 1.1–10.0 equivalents, of triethylsilane. The reaction mixture is stirred at about ambient temperature for from about 1 to about 48 hours at which time the reaction mixture is concentrated under reduced pressure. The residue is then treated with 2N sodium or potassium hydroxide and the mixture extracted with a water immiscible solvent such as dichloromethane or diethyl ether. The resultant 4-arylpiperidine is purified by column chromatography if desired.

Compounds of the invention where n=1 may be prepared by reacting an appropriate aryllithium with a 4-formylpiperidine as illustrated in Synthetic Scheme II where Aryl, $R^{1*}$, halide, and $R^2$ are as previously defined.

Synthetic Scheme II

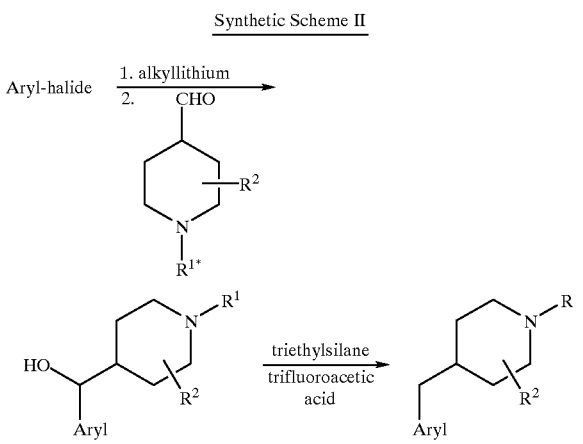

The alkyllithium, generated as described supra or by direct deprotonation of an aryl substrate, is reacted with the aldehyde to provide a the corresponding tertiary alcohol. This alcohol is then treated with triethylsilane in trifluoroacetic acid at room temperature until the dehydroxylation is complete, typically from about 1 to about 16 hours.

Compounds of the invention where the tetrahydropyridine or piperidine ring is connected to the Aryl ring at a position adjacent to a nitrogen atom may be prepared by the coupling procedure illustrated in Synthetic Scheme III where Aryl** is indazol-3-yl, benzimidazol-2-yl, benzothiazol-3-yl, benzoxazol-2-yl, benzoisothiazol-3-yl, benzoisoxazol-3-yl, quinolin-2-yl, isoquinolin-1-yl or isoquinolin-3-yl; and $R^{1*}$, halide, and $R^2$ are as previously defined.

Synthetic Scheme III

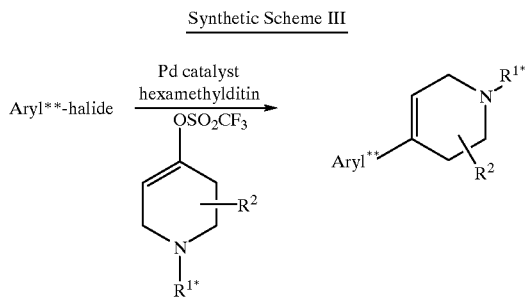

The aryl halide, typically an aryl chloride, is reacted with an appropriate triflate in the presence of a palladium catalyst, typically tetrakis [triphenylphosphine]palladi-um(0), hexamethylditin, and lithium chloride under the conditions described by S. Hitchcock et al., *Tetrahedron Letters*, 36, 9085 (1995). The 1,2,3,6-tetrahydropyridines prepared by this method may be further reacted as described in Synthetic Scheme I to prepare additional compounds of the invention.

The skilled artisan will appreciate that not all of the optional Aryl substituents will survive the anion chemistry described supra. The preparation of compounds containing functionality sensitive to anion chemistry may be accomplished by the use of an appropriate amino-substituted substrate. Once the anion chemistry is completed, the amino group may be diazotized and displaced under standard methods to provide the appropriate halo or cyano substituted compound. The nitrile may be hydrated to the carboxamide if desired.

The skilled artisan will also appreciate that where $R^{1*}$ is a nitrogen protecting group, the nitrogen protecting group may be removed at any convenient point in the synthesis. Furthermore, deprotection may be accomplished simultaneously with functional group transformations under the acidic conditions required for dehydration or during hydrogenation of the 1,2,3,6-tetrahydropyridine ring depending upon the specific protecting group employed.

The following preparations and examples further illustrate the synthesis of the compounds of this invention and are not intended to limit the scope of the invention in any way. The compounds described below were identified by various standard analytical techniques as stated in the individual preparations and examples.

PREPARATION I 1-phenoxycarbonyl-2-methyl-1,2,3,4-tetrahydropiperidin-4-one

A solution of 1.5 gm (13.7 mmol) 4-methoxypyridine and 4.6 mL (13.7 mMol) methylmagnesium chloride in 30 mL tetrahydrofuran was cooled to −23° C. at which time 1.72 mL (13.7 mMol) phenyl chloroformate was added. The reaction mixture was stirred for 20 minutes and was then poured into 10% hydrochloric acid and stirred for at room temperature for 10 minutes. This mixture was then extracted well with diethyl ether. The ether extracts were combined, washed with saturated aqueous sodium chloride, dried over sodium sulfate and concentrated under reduced pressure. The residue was subjected to flash silica gel chromatography, eluting with 9:1 hexane:ethyl acetate. Fractions containing product were combined and concentrated under reduced pressure to provide 1.54 gm (49%) of the title compound as a white solid.

PREPARATION II 1,2-dimethylpiperidin-4-one

Ethyl 3-(N-methylamino)butanoate

A solution of 479.2 mL (0.958 mole) methylamine (2M in tetrahydrofuran) was added dropwise to 99.44 gm ethyl crotonate with stirring. After stirring 5 days at room temperature the reaction mixture was concentrated under reduced pressure to remove tetrahydrofuran. The residue was distilled to provide 91.25 gm (72%) of the desired product in 2 fractions. MS(FD): m/e=145 (M+); EA: Calculated for: $C_7H_{15}NO_2$: Theory: C, 57.90; H, 10.41; N, 9.65. Found: C, 57.61; H, 10.66; N, 9.88.

Ethyl 3-(N-methyl-N-(2-ethoxycarbonyleth-1-yl)amino) butanoate

A mixture of 54.4 gm (0.374 mole) ethyl 3-(N-methyl-amino)butanoate and 100 gm (0.999 mole) ethyl acrylate was heated at 110° C. with stirring for 18 hours. The reaction mixture was cooled to room temperature and then distilled under reduced pressure to provide 61.7 gm (67.1%) of the desired compound.

b.p.=93–100° C. (0.12 mm Hg); MS(FD): M/e=245 (M+); EA: Calculated for: $C_{12}H_{23}NO_4$: Theory: C, 58.75; H, 9.45; N, 5.71. Found: C, 59.02; H, 9.65; N, 6.00.

Cyclization/decarboxylation

A solution of 43.0 gm (0.175 mole) ethyl 3-(N-methyl-N-(2-ethoxycarbonyleth-1-yl)amino)butanoate in 150 mL benzene was added dropwise to a stirring suspension of 5.6 gm (0.14 mole) sodium hydride (60% dispersion in mineral oil) in 100 mL benzene at room temperature. To this gelatinous mixture were added an additional 250 mL benzene and 3.5 gm (0.088 mole) sodium hydride (60% dispersion in mineral oil) and the mixture heated to reflux for 2 hours. The reaction mixture was then cooled to room temperature and acidified by the addition of concentrated hydrochloric acid. The phases were separated and the organic phase extracted with 3×100 mL 5N hydrochloric acid. The combined aqueous phases were allowed to stand at room temperature for 18 hours and were then heated to reflux for 4 hours. The reaction mixture was cooled to 0° C. and basified (pH⁻14) with 50% aqueous NaOH. The mixture was extracted with 4×200 mL dichloromethane. The combined organic extracts were dried over sodium sulfate and then concentrated under reduced pressure to provide 22.2 gm of a brown oil. This residual oil was subjected to silica gel chromatography, eluting with 5% methanol in dichloromethane containing a trace of ammonium hydroxide. Fractions shown to contain product were combined and concentrated under reduced pressure to provide 18.7 gm of an oil. This oil was fractionally distilled to provide 10.2 gm (46%) of the title compound.

MS(FD): M/e=127 (M⁺); EA: Calculated for: $C_7H_{13}NO$: Theory: C, 66.10; H, 10.30; N, 11.01. Found: C, 65.80; H, 10.44; N, 11.04.

PREPARATION III

1-phenoxycarbonyl-2-methyl-4-trifluoromethanesulfonyloxy-1,2,3,6-tetrahydropyridine A solution of 11.47 gm (49.8 mMol) 1-phenoxycarbonyl-2-methyl-1,2,3,4-tetrahydropiperidin-4-one in tetrahydrofuran was cooled to −23° C. at which point 54.8 mL (54.8 mMol) L-Selectride (1.0 M in tetrahydrofuran) was added dropwise via an additional funnel. The reaction mixture was stirred for two hours and then a solution of 18.69 gm (52.3 mMol) N-phenyltrifluoromethanesulfonimide in tetrahydrofuran was added dropwise and the resulting mixture stirred at room temperature for 18 hours. The reaction mixture was then concentrated under reduced pressure and the residue dissolved in diethyl ether. The ether extracts were combined, washed with saturated aqueous sodium chloride, dried over magnesium sulfate and concentrated under reduced pressure. The residue was subjected to flash silica gel chromatography, eluting with 9:1 hexane:ethyl acetate. Fractions containing product were combined and concentrated under reduced pressure to provide 9.46 gm (52%) of the title compound as a yellow oil.

PREPARATION IV

1-tert-butoxycarbonyl-4-formylpiperidine

A solution of 25 gm (159 mMol) ethyl piperidine-4-carboxylate in 240 mL dioxane and 160 mL water was first cooled to 0° C., and then 33.7 gm (318 mMol) sodium carbonate and 38 gm (175 mMol) di-tert-butyldicarbonate were added. After stirring at room temperature for 18 hours, the reaction mixture was concentrated under reduced pressure. The residue was dissolved in ethyl acetate and the mixture was treated with 1.5 M aqueous sodium hydrogen sulfate until the pH was about 2. The phases were separated and the organic phase was washed with saturated aqueous sodium chloride, dried of over sodium sulfate, and concentrated to provide 39.2 gm (96%) ethyl 1-tert-butoxycarbonylpiperidine-4-carboxylate as a clear oil.

To a solution of 39.2 gm (152 mMol) ethyl 1-tert-butoxycarbonylpiperidine-4-carboxylate in 600 mL diethyl ether were cautiously added 6.1 gm (152 mMol) lithium aluminum hydride in portions. The reaction mixture was stirred for about 1.5 hours after the addition was complete and was then carefully quenched with water. The reaction mixture was partitioned between diethyl ether and 5 N sodium hydroxide. The organic phase was washed with saturated aqueous sodium chloride, dried over magnesium sulfate, and concentrated under reduced pressure to provide about 24 gm of a waxy solid. This solid was crystallized from a mixture of diethyl ether and hexane to provide 11.7 gm (36%) of 1-tert-butoxycarbonyl-4-hydroxymethylpiperidine as a white solid.

A solution of 1.8 mL (20.4 mMol) oxalyl chloride in 180 mL dichloromethane was cooled to −60° C. at which point 2.9 mL (40.9 mMol) dimethylsulfoxide was added. After stirring for about 5 minutes, a solution of 4.0 gm (18.6 mmol) 1-tert-butoxycarbonyl-4-hydroxymethylpiperidine in dichloromethane was added. After stirring for 20 minutes, 12.9 mL (92.9) mmol triethylamine were added and the resulting solution was allowed to warm to room temperature and was stirred at that temperature for about an hour. The reaction mixture was partitioned between ethyl acetate and saturated aqueous sodium chloride. The organic phase was washed sequentially with 5 N hydrochloric acid and saturated aqueous sodium chloride, dried over sodium sulfate, and concentrated under reduced pressure to provide 3.76 gm (95%) of the title compound as a yellow oil.

PREPARATION V

Naphthalene-2-boronic acid

A solution of 15 gm (63.3 mMol) 2-bromonaphthalene in 100 mL tetrahydrofuran was cooled to −78° C. and then 47.4 mL (75.9 mMol) n-butyllithium (1.6 M in hexane) were added. After stirring for about 1.5 hours, a solution of 19 mL (82.2 mMol) triisopropylborate in 30 mL tetrahydrofuran was added via addition funnel. The reaction mixture was allowed to warm to room temperature and was stirred for about 18 hours. The reaction mixture was then partitioned between ethyl acetate and 2 N hydrochloric acid. The phases were separated and the organic phase washed with saturated aqueous sodium chloride, dried over sodium sulfate and concentrated under reduced pressure. The residual solid was suspended in hexanes and the mixture subjected to sonication. The suspension was then filtered to provide 8.3 gm (76%) of the title compound as a white solid.

EXAMPLE 1

4-(naphth-1-yl)piperidine
1-benzyl-4-hydroxy-4-(naphth-1-yl)piperidine

A solution of 10.0 gm (42.2 mMol) 1-bromonaphthalene in 180 mL tetrahydrofuran was cooled to −78° C. and then to this solution were added 48.7 mL (63.3 mMol) sec-butyllithium (1.3 M in cyclohexane). After stirring for about 1.5 hours, a solution of 8.2 mL (44.3 mMol) 1-benzylpiperidin-4-one in 60 mL tetrahydrofuran was added dropwise and the resulting mixture was allowed to warm gradually to room temperature. The reaction was then quenched by the addition of 2 N sodium hydroxide. The resulting mixture was extracted with diethyl ether. The organic extracts were combined, washed with saturated aqueous sodium chloride, and concentrated under reduced pressure. The residue was subjected to flash silica gel chromatography, eluting with dichloromethane containing from 0 to 2% methanol. Fractions containing product were combined and concentrated under reduced pressure to provide 4.34 gm (32%) of the desired compound as a white foam.

1-benzyl-4-(naphth-1-yl)-1,2,3,6-tetrahydropyridine

A mixture of 2.8 gm (8.8 mMol) 1-benzyl-4-hydroxy-4-(naphth-1-yl)piperidine and 3.36 gm (17.6 mMol)

p-toluenesulfonic acid in 50 mL toluene was heated at reflux for about 18 hours. The reaction mixture was then cooled to room temperature and partitioned between ethyl acetate and 2 N sodium hydroxide. The phases were separated and the organic phase was washed with saturated aqueous sodium chloride, dried over sodium sulfate and concentrated under reduced pressure to provide 2.47 gm (94%) of the desired compound as an orange oil.

Reduction/hydrogenolysis

A mixture of 2.47 gm (8.2 mMol) 1-benzyl-4-(naphth-1-yl)-1,2,3,6-tetrahydropyridine and 5% palladium on carbon in 60 mL ethanol and 15 mL trifluoroethanol was stirred at room temperature under about 1 atmosphere of hydrogen for 48 hours. The reaction mixture was filtered through a bed of CELITE® and the filtrate was concentrated under reduced pressure. The residue was subjected to flash silica gel chromatography, eluting with dichloromethane containing 5% methanol and 1% ammonium hydroxide. Fractions containing product were combined and concentrated under reduced pressure to provide 0.80 gm (46%) of the title compound as a tan waxy solid.

m.p.=72–74° C.; MS(FD): m/e=211 ($M^+$); EA: Calculated for $C_{15}H_{17}N$: Theory: C, 85.26; H, 8.11; N, 6.63. Found: C, 85.03; H, 8.17; N, 6.62.

EXAMPLE 2

4-(naphth-2-yl)piperidine

Beginning with 6.0 gm (29 mMol) 2-bromonaphthalene, the title compound was prepared substantially as described in EXAMPLE 1.

EXAMPLE 3

4-(6-hydroxynaphth-2-yl)piperidine

A mixture of 9.42 gm (47.1 mMol) potassium hydride (35 wt. % dispersion in mineral oil) in 180 mL tetrahydrofuran was cooled to 0° C. and then 10.0 gm (44.8 mMol) 6-hydroxy-2-bromonaphthalene were added and the reaction mixture was stirred for 2 hours. The reaction mixture was then cooled to −78° C. and then 58 mL (98.6 mMol) tert-butyllithium (1.7 M in pentane) were added. The resulting solution was reacted as described in EXAMPLE 1 to provide 0.156 gm of the title compound as a tan solid.

MS(FD): m/e=227 ($M^+$);

EXAMPLE 4

Sodium 4-(6-naphth-2-yloxy)-1,2,3,6-tetrahydropyridine hydrate 1-benzyl-4-hydroxy-4-(6-methoxynaphth-2-yl)piperidine A solution of 5.0 gm (21.1 mMol) 6-methoxy-4-bromonaphthalene in 120 mL tetrahydrofuran was first cooled to −78° C. and then 27.3 mL (46.4 mMol) tert-butyllithium (1.7 M in pentane) were added and the resulting solution stirred for about 1.5 hours. At this point a solution of 4.1 mL (22.1 mMol) 1-benzylpiperidin-4-one in 30 mL tetrahydrofuran was added and the reaction mixture was allowed to warm gradually to room temperature. After 3 hours the reaction was quenched by the addition of 2 N sodium hydroxide. The resulting mixture was extracted with diethyl ether. The organic extracts were combined, washed with saturated aqueous sodium chloride, and concentrated under reduced pressure. The residue was subjected to flash silica gel chromatography, eluting with dichloromethane containing from 0 to 2% methanol. Fractions containing product were combined and concentrated under reduced pressure. The residue was crystallized from ethyl acetate to provide 4.62 gm (63%) of the desired compound as a white solid.

4-hydroxy-4-(6-methoxynaphth-2-yl)-piperidine

A mixture of 1.0 gm (2.9 mMol) 1-benzyl-4-hydroxy-4-(6-methoxynaphth-2-yl)piperidine and 5% palladium on carbon in 20 mL methanol was stirred at room temperature under about 1 atmosphere of hydrogen for 6 hours. The reaction mixture was filtered through a bed of CELITE® and the filtrate was concentrated under reduced pressure to provide 0.64 gm (86%) of the desired compound as a white foam. A portion of the material was converted to the oxalate salt for analysis.

m.p.=213–215° C.; MS(FD): m/e=257 ($M^+$); EA: Calculated for $C_{16}H19NO_2$—$C_2H_2O_4$: Theory: C, 62.24; H, 6.09; N, 4.03. Found: C, 62.17; H, 6.05; N, 3.87.

Dehydration/demethylation

A mixture of 5.47 gm (21 mMol) 4-hydroxy-4-(6-methoxynaphth-2-yl)piperidine and 8.4 mL (74 mMol) 48% hydrobromic acid in acetic acid was stirred at reflux until the reaction was complete. The reaction mixture was cooled to room temperature and then concentrated under reduced pressure. The residue was treated with 2N sodium hydroxide resulting in the formation of a solid. The suspension was filtered and the filter cake washed with toluene followed by diethyl ether to provide 4.5 gm (94%) of the title compound as a grey solid.

m.p.=267–268° C.; MS(FD): m/e=225 ($M^+$); EA: Calculated for $C_{15}H_{15}NONa$-0.75 $H_2O$: Theory: C, 69.09; H, 5.99; N, 5.37. Found: C, 69.35; H, 6.06; N, 5.31.

EXAMPLE 5

4-(6-methoxynaphth-2-yl)-1,2,3,6-tetrahydropyridine hydrate 1-tert-butoxgcarbonyl-4-hydroxy-4-(6-methoxynaphth-2-yl)piperidine Beginning with 5.68 gm (23.9 mMol) 6-methoxy-2-bromonaphthalene and 5.01 gm (25.2 mMol) 1-tert-butoxycarbonylpiperidin-4-one, 6.15 gm (72%) of the title compound were recovered from a mixture of ethyl acetate and hexane as a white solid essentially by the procedure described in EXAMPLE 1.

Dehydration/deprotection

A mixture of 2.0 gm (5.6 mMol) 1-tert-butoxycarbonyl-4-hydroxy-4-(6-methoxynaphth-2-yl)piperidine and 3.41 gm (17.9 mMol) p-toluenesulfonic acid in 60 mL toluene was heated at reflux for 18 hours. The reaction mixture was cooled to room temperature and partitioned between ethyl acetate and 2N sodium hydroxide. The phases were separated and the organic phase washed with saturated aqueous sodium chloride, dried over sodium sulfate, and concentrated under reduced pressure. The residue was subjected to flash silica gel chromatography, eluting with dichloromethane containing 10% methanol. Fractions containing product were combined and concentrated under reduced pressure to provide 0.41 gm of the title compound as a tan solid.

MS(FD): m/e=239 ($M^+$); EA: Calculated for $C_{16}H_{17}NO$-0.25 $H_2O$: Theory: C, 78.87; H, 7.23; N, 5.74. Found: C, 78.71; H, 7.06; N, 5.57.

EXAMPLE 6

4-(6-methoxynaphth-2-yl)piperidine

Beginning with 5.0 gm (21.1 mMol) 6-methoxy-2-bromonaphthalene and 4.1 mL (22.1 mMol)

1-benzylpiperidin-4-one, the title compound was recovered as a white solid substantially by the procedure described in EXAMPLE 1.

m.p.=123–125° C.; MS(FD): m/e=241 (M⁺); EA: Calculated for $C_{16}H_{19}NO$: Theory: C, 79.63; H, 7.94; N, 5.80. Found: C, 79.58; H, 7.78; N, 5.54.

EXAMPLE 7

4-(6-methylnaphth-2-yl)-1,2,3,6-tetrahydropyridine 1-benzyl-4-(6-hydroxynaphth-2-yl)-1,2,3,6-tetrahydropyridine A solution of 1.0 gm (2.9 mMol) 1-benzyl-4-hydroxy-4-(6-methoxynaphth-2-yl)piperidine and 0.65 mL (5.8 mMol) 48% hydrobromic acid in 10 mL acetic acid was heated at reflux for 18 hours. The reaction mixture was cooled to room temperature, neutralized with 5N sodium hydroxide, and extracted well with ethyl acetate. The organic extracts were combined, washed with saturated aqueous sodium chloride, dried over sodium sulfate, and concentrated under reduced pressure. The residual solid was suspended in a mixture of ethyl acetate and hexane and the suspension sonicated. The suspension was then filtered to provide 0.57 gm (63%) of the desired compound as a grey solid.

1-benzyl-4-(6-trifluoromethanesulfonyloxynaphth-2-yl)-1,2,3,6-tetrahydropyridine A solution of 4.59 gm (14.6 mMol) 1-benzyl-4-(6-hydroxynaphth-2-yl)-1,2,3,6-tetrahydropyridine in 20 mL pyridine was first cooled to 0° C. and then 2.9 mL (17.5 mMol) trifluoromethanesulfonic anhydride were added dropwise. The reaction mixture was stirred for 18 hours at room temperature and then another 1.2 mL of trifluoromethanesulfonic anhydride were added. Once the reaction was complete the reaction mixture was poured into water and extracted well with ethyl acetate. The organic phases were combined, washed with saturated aqueous sodium chloride, dried over sodium sulfate, and concentrated under reduced pressure. The residue was subjected to flash silica gel chromatography, eluting with hexane containing 20% ethyl acetate. Fractions containing product were combined and concentrated under reduced pressure to provide 4.97 gm (76%) of the desired compound as a light yellow oil which solidified upon standing in the refrigerator.

1-benzyl-4-(6-methylnaphth-2-yl)-1,2,3,6-tetrahydropyridine

A solution of 0.50 gm (1.1 mMol) 1-benzyl-4-(6-trifluoromethanesulfoxynaphth-2-yl)-1,2,3,6-tetrahydropyridine and 0.030 gm (0.06 mMol) nickel(II) chloride (1,2-bis(diphenylphosphino)methane) in 10 mL diethyl ether was first cooled to 0° C. and then 0.74 mL (2.2 mMol) methylmagnesium bromide (3 M in diethyl ether) were added and the reaction mixture was stirred for 18 hours at room temperature. An additional 1.11 mL (3.3 mMol) methylmagnesium bromide were added and the reaction stirred an additional 18 hours at room temperature. The reaction mixture was then quenched by the addition of saturated aqueous ammonium chloride. The resulting mixture was extracted well with ethyl acetate. The organic phases were combined, washed with saturated aqueous sodium chloride, dried over sodium sulfate, and concentrated under reduced pressure. The residue was subjected to flash silica gel chromatography, eluting with hexane containing 5% ethyl acetate. Fractions containing product were combined and concentrated under reduced pressure to provide 0.244 gm (70%) of the desired compound as a waxy solid.

MS(FD): m/e=313 (M⁺).

Debenzylation

A mixture of 0.989 gm (3.2 mMol) 1-benzyl-4-(6-methylnaphth-2-yl)-1,2,3,6-tetrahydropyridine in 15 mL 1,2-dichloroethane was cooled to 0° C. and to this mixture were gradually added 1.36 mL (12.6 mMol) α-chloroethyl chloroformate. The reaction mixture was allowed to warm gradually to room temperature and was stirred at reflux for about 18 hours. The reaction mixture was cooled to room temperature and then concentrated under reduced pressure. The residue was dissolved in 40 mL methanol and this solution stirred at reflux for 4 hours. The mixture was cooled to room temperature and concentrated under reduced pressure. The residue was partitioned between 100 mL ethyl acetate and 50 mL 2N sodium hydroxide. The phases were separated and the organic phase was washed with saturated aqueous sodium chloride, dried over sodium sulfate and concentrated under reduced pressure. The residue was subjected to flash silica gel chromatography, eluting with dichloromethane containing 9% methanol. Fractions containing product were combined and concentrated under reduced pressure to provide 0.439 gm (63%) of the title compound as a tan solid. A portion was converted to the oxalate salt for analysis.

m.p.=206–209° C.; MS(FD): m/e=223 (M⁺); EA: Calculated for $C_{16}H_{17}NO_2$—$C_2H_2O_4$: Theory: C, 69.00; H, 6.11; N, 4.47. Found: C, 69.11; H, 6.23; N, 4.58.

EXAMPLE 8

4-(6-methylnaphth-2-yl)piperidine 1-benzyl-4-(6-methoxynaphth-2-yl)-piperidine

A mixture of 2.92 gm 1-benzyl-4-(6-methoxynaphth-2-yl)-1,2,3,6-tetrahydropyridine and 0.3 gm platinum oxide in 50 mL tetrahydrofuran and 50 mL ethyl acetate was hydrogenated at room temperature for 16 hours at an initial hydrogen pressure of 60 p.s.i. The reaction mixture was filtered and the filtrate concentrated under reduced pressure to provide 2.71 gm of the title compound as a white solid.

1-benzyl-4-(6-hydroxynaphth-2-yl)-piperidine

A mixture of 2.66 gm (8.0 mMol) 1-benzyl-4-(6-methoxynaphth-2-yl)piperidine and 2.3 mL (20 mMol) 48% hydrobromic acid in 15 mL acetic acid was stirred at reflux for about 18 hours. The reaction mixture was cooled and then neutralized by the addition of 5N sodium hydroxide. The mixture was extracted well with ethyl acetate and the combined organic extracts were washed with saturated aqueous sodium chloride, dried over sodium sulfate, and concentrated under reduced pressure. The residue was suspended in a mixture of hexane and ethyl acetate and this suspension was subjected to sonication. The suspension was then filtered to provide 2.02 gm (79%) of the desired compound as a tan solid.

1-benzyl-4-(6-trifluoromethanesulfonyloxynaphth-2-yl)piperidine

Beginning with 2.02 gm (6.4 mMol) 1-benzyl-4-(6-hydroxynaphth-2-yl)piperidine, 1.69 gm (59%) of the desired compound were prepared as a waxy solid substantially by the procedure of EXAMPLE 7.

1-benzyl-4-(6-methylnaphth-2-yl)piperidine

Beginning with 0.800 gm (1.8 mMol) 1-benzyl-4-(6-trifluoromethanesulfonyloxynaphth-2-yl)piperidine, 0.400 gm (71%) of the desired compound were prepared as a waxy solid substantially by the procedure of EXAMPLE 7.

Hydrogenolysis

Beginning with 0.385 gm (1.2 mMol) 1-benzyl-4-(6-methylnaphth-2-yl)piperidine, 0.136 gm (49%) of the title compound were prepared as a white solid substantially by the procedure of EXAMPLE 1.

MS(FD): m/e=225 (M$^+$).

EXAMPLE 9

4-(6-ethylnaphth-2-yl)piperidine
1-benzyl-4-(6-vinylnaphth-2-yl)piperidine

Beginning with 0.839 gm (1.9 mMol) 1-benzyl-4-(6-trifluoromethanesulfonyloxynaphth-2-yl)piperidine and 3.73 mL (3.7 mMol) vinylmagnesium bromide (1M in tetrahydrofuran), 0.394 gm (65%) of the desired compound were prepared as a waxy white solid substantially by the procedure of EXAMPLE 7.

Reduction/Hydrogenolysis

Beginning with 0.394 gm (1.2 mMol) 1-benzyl-4-(6-vinylnaphth-2-yl)piperidine, 0.155 gm (54%) of the title compound were prepared as a white solid substantially by the procedure of EXAMPLE 1.

m.p.=112–114° C.; MS(FD): m/e=239 (M$^+$).

EXAMPLE 10 cis-2-methyl-4-(naphth-2-yl)piperidine trans-2-methyl-4-(naphth-2-yl)piperidine
1-phenoxycarbonyl-2-methyl-4-(naphth-2-yl)-1,2,3,6-tetrahydropyridine A mixture of 5.46 gm (31.8 mMol) naphthalene-2-boronic acid, 8.28 gm (22.7 mMol) 1-phenoxycarbonyl-2-methyl-4-trifluoromethanesulfonyloxy-1,2,3,6-tetrahydropyridine, 0.741 gm (0.91 mMol) palladium(II) diphenylphosphinoferrocenyl chloride, and 2.88 gm (68 mMol) lithium chloride in 25 mL 2M aqueous sodium carbonate and 96 mL dimethoxyethane was heated at reflux for about 18 hours. The reaction mixture was cooled to room temperature and was diluted with ethyl acetate and saturated aqueous sodium carbonate. The phases were separated and the organic phase was washed with saturated aqueous sodium chloride, dried over sodium sulfate and concentrated under reduced pressure. The residue was subjected to flash silica gel chromatography, eluting with hexane containing 10% ethyl acetate. Fractions containing product were combined and concentrated under reduced pressure to provide 3.87 gm (50%) of the title compound as a viscous oil.

cis- and trans-1-phenoxycarbonyl-2-methyl-4-(naphth-2-yl)piperidine

A mixture of 3.87 gm (11.3 mMol) 1-phenoxycarbonyl-2-methyl-4-(naphth-2-yl)-1,2,3,6-tetrahydropyridine and a catalytic amount of 5% palladium on carbon in 50 mL methanol was stirred at room temperature under about 1 atmosphere of hydrogen for about 18 hours. The reaction mixture was filtered through a bed of CELITE® and then concentrated under reduced pressure to provide 3.42 gm (88%) of the desired compound as a viscous oil.

Deprotection and separation of cis-/trans-isomers

A mixture of 3.42 gm (9.9 mMol) cis- and trans-1-phenoxycarbonyl-2-methyl-4-(naphth-2-yl)piperidine and 59 gm potassium hydroxide in 75 mL isopropanol and 75 mL water was stirred at reflux for 72 hours. The reaction mixture was cooled and diluted with ethyl acetate. The phases were a separated and the organic phase was washed with saturated aqueous sodium chloride, dried over sodium sulfate and concentrated under reduced pressure. The residue was subjected to flash silica gel chromatography, eluting with dichloromethane containing about 17% methanol.

Fractions containing the faster eluting isomer were combined and concentrated under reduced pressure to provide 0.872 gm (39%) of cis-2-methyl-4-(naphth-2-yl)piperidine as an oil. A portion was converted to the oxalate salt for analysis.

m.p.=257–259° C.; MS(FD): m/e=225 (M$^+$).

Fractions containing the slower eluting isomer were combined and concentrated under reduced pressure to provide 0.368 gm (16%) of trans-2-methyl-4-(naphth-2-yl)piperidine as an oil. A portion was converted to the oxalate salt for analysis.

MS(FD): m/e=225 (M$^+$).

EXAMPLE 11

2-methyl-4-(6-methoxynaphth-2-yl)-1,2,3,6-tetrahydropyridine
1-phenoxycarbonyl-2-methyl-4-(6-methoxynaphth-2-yl)-1,2,3,6-tetrahydropyridine Beginning with 3.72 gm (18.4 mMol) 6-methoxynaphthalene-2-boronic acid and 5.60 gm (15.3 mMol) 1-phenoxycarbonyl-2-methyl-4-trifluoromethanesulfonyloxy-1,2,3,6-tetrahydropyridine, 4.0 gm (70%) of the desired compound were prepared substantially as described in EXAMPLE 10.

Deprotection

Beginning with 3.82 gm (10.3 mMol) 1-phenoxycarbonyl-2-methyl-4-(6-methoxynaphth-2-yl)-1,2,3,6-tetrahydropyridine, 1.74 gm (67%) of the title compound were prepared as a light tan solid substantially as described in EXAMPLE 10.

EXAMPLE 12

2-ethyl-4-(naphth-2-yl)-1,2,3,6-tetrahydrotetrahydropyridine
1-phenoxycarbonyl-2-ethyl-4-(naphth-2-yl)-1,2,3,6-tetrahydropyridine Beginning with 3.62 gm (21.1 mMol) naphthalene-2-boronic acid and 5.70 gm (15.0 mMol) 1-phenoxycarbonyl-2-ethyl-4-trifluoromethanesulfonyloxy-1,2,3,6-tetrahydropyridine, 4.04 gm (75%) of the desired compound were prepared substantially as described in EXAMPLE 11.

Deprotection

Beginning with 4.04 gm (11.3 mMol) 1-phenoxycarbonyl-2-ethyl-4-(naphth-2-yl)-1,2,3,6-tetrahydropyridine, 1.41 gm (52%) of the title compound were prepared as an oily solid substantially as described in EXAMPLE 11.

EXAMPLE 13

1-tert-butoxycarbonyl-4-(naphth-2-yl)methylpiperidine
1-tert-butoxycarbonyl-4-(α-(naphth-2-yl)-α-(hydroxy)-methyl)piperidine Beginning with 2.0 gm (9.7 mMol) 2-bromonaphthalene and 2.16 gm (10.1 mMol) 1-tert-butoxycarbonyl-4-formylpiperi-dine, 1.9 gm (58%) of the desired compound were prepared as an off-white solid substantially by the procedure as described in EXAMPLE 1.

Dehydroxylation/deprotection

A mixture of 1.9 gm (5.6 mMol) 1-tert-butoxycarbonyl-4-(α-(naphth-2-yl)-α-(hydroxy)methyl)piperidine, 2.2 mL (13.9 mMol) triethylsilane, and 15 mL trifluoroacetic acid was stirred at room temperature for about 2 hours. The reaction mixture was concentrated under reduced pressure and the residue partitioned between ethyl acetate and 5N hydrochloric acid. The aqueous phase was extracted with two volumes of ethyl acetate. The remaining aqueous phase was made basic by the addition of 5N sodium hydroxide, and was then extracted well with ethyl acetate. These ethyl acetate extracts were combined, washed with saturated aqueous sodium chloride, dried over sodium sulfate and concentrated under reduced pressure. The residue was subjected to flash silica gel chromatography, eluting with dichloromethane containing about 17% methanol. Fractions containing product were combined and concentrated under reduced pressure to provide 0.862 gm (69%) of the title compound as a white waxy solid.

A portion of the product was converted to the oxalate salt for analysis.

m.p.=186° C.; MS(FD): m/e=225 (M$^+$); EA: Calculated for $C_{16}H_{19}N$—$C_2H_2O_4$: Theory: C, 68.55; H, 6.71; N, 4.44. Found: C, 68.49; H, 6.71; N, 4.26.

EXAMPLE 14

4-(quinolin-2-yl)-1,2,3,6-tetrahydropyridine 1-tert-butoxycarbonyl-4-(quinolin-2-yl)-1,2,3,6-tetrahydropyridine A mixture of 0.800 gm (4.9 mMol) 2-chloroquinoline, 1.62 gm (4.9 mMol) 1-tert-butoxy-4-trifluoromethanesulfonyl-oxy-1,2,3,6-tetrahydropyridine, 1.75 gm (4.9 mMol) hexamethylditin, 0.622 gm (14.7 mMol) anhydrous lithium chloride, and 0.283 gm (0.24 mMol) tetrakis [triphenylphos-phine]palladium(0) in dioxane was stirred at reflux for about 16 hours. The reaction mixture was cooled to room temperature and then poured into saturated aqueous potassium fluoride. The mixture was then diluted with ethyl acetate and stirred for about 2 hours. The phases were separated and the organic phase washed with saturated aqueous sodium chloride, dried over magnesium sulfate, and concentrated under reduced pressure. The residue was subjected to flash silica gel chromatography, eluting with hexane containing about 6% ethyl acetate. Fractions containing product were combined and concentrated under reduced pressure to provide 0.632 gm of the desired compound as a light yellow oil.

Deprotection

A mixture of 0.632 gm (2.0 mMol) 1-tert-butoxycarbonyl-4-(quinolin-2-yl)-1,2,3,6-tetrahydropyridine, 5 mL trifluoroacetic acid, a drop of thiophenol, and 5 mL dichloromethane was stirred at room temperature for about 5 hours. The reaction mixture was concentrated under reduced pressure and the residue partitioned between ethyl acetate and 2N sodium hydroxide. The phases were separated and the organic phase washed with saturated aqueous sodium chloride, dried over sodium sulfate, and concentrated under reduced pressure to provide 0.268 gm (63%) of the title compound as a light yellow wax.

A portion was converted to the oxalate salt for analysis.

MS(FD): m/e=210 (M$^+$); EA: Calculated for $C_{14}H_{14}N_2$—$C_2H_2O_4$: Theory: C, 63.99; H, 5.37; N, 9.33. Found: C, 64.13; H, 5.60; N, 9.57.

EXAMPLE 15

4-(4-chlorobenzothiazol-2-yl)-1,2,3,6-tetrahydropyridine 1-tert-butoxycarbonyl-4-(4-chlorobenzothiazol-2-yl)-1,2,3,6-tetrahydropyridine Beginning with 2.0 gm (10 mMol) 2,4-dichlorobenzothiazole and 3.58 gm (10.8 mMol) 1-tert-butoxy-4-trifluoromethanesulfonyloxy-1,2,3,6-tetrahydropyridine, 2.16 gm (63%) of the desired compound were prepared as a light yellow waxy solid substantially by the procedure described in EXAMPLE 14.

m.p.=98–101° C.; EA: Calculated for $C_{17}H_{19}N_2O_2SCl$: Theory: C, 58.20; H, 5.46; N, 7.98. Found: C, 58.43; H, 5.55; N, 8.01.

Deprotection

Beginning with 0.805 gm (2.3 mMol) 1-tert-butoxycarbonyl-4-(4-chlorobenzothiazol-2-yl)-1,2,3,6-tetrahydropyridine, 0.497 gm (86%) of the title compound were prepared as an off-white solid substantially by the procedure described in EXAMPLE 14.

m.p.=112–114° C.; MS(FD): m/e=250 (M$^+$); EA: Calculated for $C_{12}H_{11}N_2SCl$: Theory: C, 57.48; H, 4.42; N, 11.17. Found: C, 57.78; H, 4.48; N, 11.04.

EXAMPLE 16

4-(6-chlorobenzothiazol-2-yl)-1,2,3,6-tetrahydropyridine 1-tert-butoxycarbonyl-4-(6-chlorobenzothiazol-2-yl)-1,2,3,6-tetrahydropyridine Beginning with 2.0 gm (10 mMol) 2,6-dichlorobenzothiazole and 3.91 gm (11.8 mMol) 1-tert-butoxy-4-trifluoromethanesulfonyloxy-1,2,3,6-tetrahydropyridine, 1.77 gm (51%) of the desired compound were prepared as a waxy solid substantially by the procedure described in EXAMPLE 14. EA: Calculated for $C_{17}H_{19}N_2O_2SCl$: Theory: C, 58.20; H, 5.46; N, 7.98. Found: C, 57.90; H, 5.48; N, 8.01.

Deprotection

Beginning with 0.408 gm (1.2 mMol) 1-tert-butoxycarbonyl-4-(6-chlorobenzothiazol-2-yl)-1,2,3,6-tetrahydropyridine, 0.158 gm (54%) of the title compound were prepared as an off-white solid substantially by the procedure described in EXAMPLE 14.

m.p.=125° C.; MS (FD): m/e=250 (M$^+$); EA: Calculated for $C_{12}H_{11}N_2SCl$: Theory: C, 57.48; H, 4.42; N, 11.17. Found: C, 57.19; H, 4.63; N, 11.01.

EXAMPLE 17

4-(6-chlorobenzothiazol -2-yl) piperidine 1-tert -butoxycarbonyl-4-(6-chlorobenzothiazol-2-yl) piperidine A mixture of 0.939 gm (2.7 mMol) 1-tert-butoxycarbonyl-4-(6-chlorobenzothiazol-2-yl)-1,2,3,6-tetrahydropyridine and a catalytic amount of platinum oxide in 20 mL methanol was stirred at room temperature under about 1 atmosphere of hydrogen for about 3 hours. The reaction mixture was concentrated under reduced pressure, the residue dissolved in a minimal volume of ethyl acetate, and the mixture filtered through a bed of flash silica gel, eluting with 1:1 hexane:ethyl acetate. The filtrate was concentrated under reduced pressure to provide 0.663 gm (70%) of the desired compound as a light tan oil.

Deprotection

Beginning with 0.663 gm (1.9 mMol) 1-tert-butoxycarbon-yl-4-(6-chlorobenzothiazol-2-yl)piperidine, 0.263 gm (55%) of the title compound were recovered as an off-white solid, substantially as described in EXAMPLE 14.

m.p.=115–117° C.; MS(FD): m/e=252 (M$^+$); EA: Calculated for $C_{12}H_{13}N_2SCl$-0.5 $H_2O$: Theory: C, 55.06; H, 5.39; N, 10.70. Found: C, 55.27; H, 5.11; N, 10.77.

EXAMPLE 18 cis- and trans-2-ethyl-4-(naphth-2-yl)piperidine

Beginning with 1.41 gm (5.9 mMol) 2-ethyl-4-(naphth-2-yl)-1,2,3,6-tetrahydropyridine, the title compounds were isolated essentially as described in EXAMPLE 10.

cis-2-ethyl-4-(naphth-2-yl)piperidine

Fractions containing the faster eluting isomer were combined and concentrated under reduced pressure to provide 0.392 gm (28%) of the cis-isomer. A portion was converted to the oxalate salt.

m.p.=186° C.; MS(FD): m/e=239 (M$^+$).

trans-2-ethyl-4-(naphth-2-yl)piperidine

Fractions containing the slower eluting isomer were combined and concentrated under reduced pressure to provide 0.387 gm (27%) of the trans-isomer. A portion was converted to the oxalate salt.

MS(FD): m/e=239 (M$^+$).

EXAMPLE 19 cis- and trans-2-methyl-4-(6-methoxynaphth-2-yl) piperidine

Beginning with 1.74 gm (6.9 mMol) 2-methyl-4-(6-methoxynaphth-2-yl)-1,2,3,6-tetrahydropyridine, the title compounds were isolated essentially as described in EXAMPLE 18.

cis-2-methyl-4-(6-methoxynaphth-2-yl)piperidine

Fractions containing the faster eluting isomer were combined and concentrated under reduced pressure to provide 0.636 gm (36%) of the cis-isomer as a waxy solid. A portion was converted to the oxalate salt.

m.p.=257–259° C.; MS(FD): m/e=255 (M$^+$).

trans-2-methyl-4-(6-methoxynaphth-2-yl)piperidine

Fractions containing the slower eluting isomer were combined and concentrated under reduced pressure to provide 0.717 gm (41%) of the trans-isomer. A portion was converted to the oxalate salt.

m.p.=183–185° C.; MS(FD): m/e=255 (M$^+$).

EXAMPLE 20 cis- and trans-2-methyl-4-(benzofur-2-yl)piperidine 1-phenoxycarbonyl-2-methyl-4-(benzofur-2-yl)-1,2,3,6-tetrahydropyridine A mixture of 2.02 gm (12.5 mMol) benzofuran-2-boronic acid, 3.5 gm (9.6 mMol) 1-phenoxycarbonyl-2-methyl-4-trifluoromethanesulfonyloxy-1,2,3,6-tetrahydropyridine, 0.443 gm (0.38 mMol) tetrakis [triphenylphosphine]-palladium(0), and 1.22 gm (28.8 mMol) lithium chloride in 55 mL dimethoxyethane and 15 mL 2M aqueous sodium carbonate was stirred at reflux for about 18 hours. The reaction mixture was cooled to room temperature and then partitioned between ethyl acetate and aqueous sodium carbonate. The phases were separated and the organic phase was washed with saturated aqueous sodium chloride, dried over sodium sulfate, and concentrated under reduced pressure. The residue was subjected to flash silica gel chromatography, eluting with hexane containing 10% ethyl acetate. Fractions containing product were combined and concentrated under reduced pressure to provide 2.87 gm (90%) of the desired compound as a light yellow oil.

cis- and trans-1-phenoxycarbonyl-2-methyl-4-(benzofur-2-yl)piperidine

Beginning with 1.73 gm (5.2 mMol) 1-phenoxycarbonyl-2-methyl-4-(benzofur-2-yl)-1,2,3,6-tetrahydropyridine, 1.19 gm (68%) of the desired compounds were prepared as a viscous oil substantially by the procedure described in EXAMPLE 10.

Deprotection and separation of cis-/trans-isomers

Beginning with 0.99 gm (3.0 mMol) cis- and trans-1-phenoxycarbonyl-2-methyl-4-(benzofur-2-yl)piperidine, the title compounds were prepared essentially as described in EXAMPLE 10.

Fractions containing the faster eluting isomer were combined and concentrated under reduced pressure to provide 0.199 gm (31%) of cis-2-methyl-4-(benzofur-2-yl) piperidine as an oil.

Fractions containing the slower eluting isomer were combined and concentrated under reduced pressure to provide 0.170 gm (27%) of trans-2-methyl-4-(benzofur-2-yl) piperidine as an oil.

MS(FD): m/e=215 (M$^+$).

EXAMPLE 21 cis- and trans-2-methyl-4-(4-fluorobenzothiazol-2-yl)piperidine 1-tert-butoxycarbonyl-2-methyl-4-(4-fluorobenzothiazol-2-yl)-1,2,3,6-tetrahydropyridine Beginning with 1.0 gm (5.4 mMol) 2-chloro-4-fluorobenzothiazole and 2.0 gm (5.66 mMol) 1-tert-butoxy-2-methyl-4-trifluoromethanesulfonyloxy-1,2,3,6-tetrahydropyridine, 1.2 gm (72%) of the desired compound were prepared as a yellow amorphous solid substantially by the procedure described in EXAMPLE 14.

MS(FD): m/e=349 (M+1); EA: Calculated for $C_{18}H_{21}N_2O_2SF$: Theory: C, 62.05; H, 6.07; N, 8.04. Found: C, 61.88; H, 5.86; N, 8.01.

Deprotection

Beginning with 1.2 gm (3.8 mMol) 1-tert-butoxycarbonyl-2-methyl-4-(4-fluorobenzothiazol-2-yl)-1,2,3,6-tetrahydropyridine, 0.79 gm (84%) of 2-methyl-4-(4-fluorobenzothiazol-2-yl)-1,2,3,6-tetrahydropyridine were prepared as a yellow oil substantially by the procedure described in EXAMPLE 14.

MS(FD): m/e=249 (M+1); EA: Calculated for $C_{13}H_{13}N_2SF$-0.2 $H_2O$: Theory: C, 61.98; H, 5.36; N, 11.12. Found: C, 62.36; H, 5.43; N, 11.33.

Reduction

A mixture of 0.69 gm (3.0 mMol) 2-methyl-4-(4-fluorobenzothiazol-2-yl)-1,2,3,6-tetrahydropyridine and 0.03 gm platinum oxide in 20 mL ethanol was hydrogenated at one atmosphere at room temperature for 20 hours. The reaction mixture was filtered and the filtrate concentrated under reduced pressure. The resulting residue was subjected to silica gel chromatography essentially as described in EXAMPLE 10.

Fractions containing the faster eluting isomer were combined and concentrated under reduced pressure to provide 0.27 gm (34%) cis-2-methyl-4-(4-fluorobenzothiazol-2-yl) piperidine.

MS(FD): m/e=251 (M+1).

Fractions containing the slower eluting isomer were combined and concentrated under reduced pressure to provide 0.24 gm (31%) trans-2-methyl-4-(4-fluorobenzothiazol-2-yl)piperidine.

MS(FD): m/e=251 (M+1); EA: Calculated for $C_{13}H_{15}N_2SF$—$H_2O$: Theory: C, 58.18; H, 6.39; N, 10.44. Found: C, 58.57; H, 6.38; N, 10.10.

EXAMPLE 22 cis- and trans-2-methyl-4-(4-methylbenzothiazol-2-yl)piperidine 1-tert-butoxycarbonyl-2-methyl-4-(4-methylbenzothiazol-2-yl)-1,2,3,6-tetrahydropyridine Beginning with 1.0 gm (5.7 mMol) 2-chloro-4-methylbenzothiazole and 2.1 gm (6.0 mMol) 1-tert-butoxy-2-methyl-4-trifluoromethanesulfonyloxy-1,2,3,6-tetrahydropyridine, 1.3 gm (66%) of the desired compound were prepared as a yellow amorphous solid substantially by the procedure described in EXAMPLE 14.

MS(FD): m/e=345 (M+1); EA: Calculated for $C_{19}H_{24}N_2O_2S$: Theory: C, 66.25; H, 7.02; N, 8.13. Found: C, 66.13; H, 7.19; N, 8.12.

Deprotection

Beginning with 1.3 gm (3.8 mMol) 1-tert-butoxycarbonyl-2-methyl-4-(4-methylbenzothiazol-2-yl)-1,2,3,6-tetrahydropyridine, 0.74 gm (85%) of 2-methyl-4-(4-methylbenzothiazol-2-yl)-1,2,3,6-tetrahydropyridine were prepared as a yellow oil substantially by the procedure described in EXAMPLE 14.

MS(FD): m/e=245 (M+1); EA: Calculated for $C_{14}H_{16}N_2S$: Theory: C, 68.81; H, 6.60; N, 11.46. Found: C, 68.60; H, 6.56; N, 11.26.

Reduction

A mixture of 0.72 gm (2.9 mMol) 2-methyl-4-(4-methylbenzothiazol-2-yl)-1,2,3,6-tetrahydropyridine and 0.7 gm platinum oxide in 25 mL ethanol was hydrogenated at one atmosphere at room temperature for 20 hours. The reaction mixture was filtered and the filtrate concentrated under reduced pressure. The resulting residue was subjected to silica gel chromatography essentially as described in EXAMPLE 10.

Fractions containing the faster eluting isomer were combined and concentrated under reduced pressure to provide 0.19 gm (27%) cis-2-methyl-4-(4-methylbenzothiazol-2-yl)piperidine.

MS(FD): m/e=246 (M+); EA: Calculated for $C_{14}H_{18}N_2S$: Theory: C, 68.25; H, 7.36; N, 11.37. Found: C, 68.45; H, 7.60; N, 11.48.

Fractions containing the slower eluting isomer were combined and concentrated under reduced pressure to provide 0.13 gm (18%) trans-2-methyl-4-(4-methylbenzothiazol-2-yl)piperidine.

MS(FD): m/e=247 (M+1); EA: Calculated for $C_{14}H_{18}N_2S$: Theory: C, 68.25; H, 7.36; N, 11.37. Found: C, 68.26; H, 7.57; N, 11.45.

The efficacy of the compounds of Formula I to inhibit the reuptake of serotonin has been determined by a paroxetine binding essay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32 M sucrose and 20 μM glucose. The preparations were resuspended after centrifugation by homogenizing in 50 volumes of cold reaction medium (50 μM sodium chloride, 50 μM potassium chloride, pH 7.4) and centrifuging at 50,000 g for 10 minutes. The process was repeated two times with a 10-minute incubation at 37° C. between the second and third washes. The resulting pellet was stored at −70° C. until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 μg protein/tube). Samples were incubated at 37° C. for 30 minutes; those containing 1 μM fluoxetine were used to determine nonspecific binding of $^3$H-paroxetine. After incubation, the tubes were filtered through Whatman GF/B filters, which were soaked in 0.05% polyethylenimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of Formula I by the above method showed potent reuptake activity, in some cases activity in the low nanomolar range.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated. It will be understood that the dosage ranges for other animals will necessarily be quite different from the doses administered to humans, and accordingly that the dosage ranges described below in the section on tobacco withdrawal must be recalculated. For example, a small dog may be only ⅒th of a typical human's size, and it will therefore be necessary for a much smaller dose to be used. The determination of an effective amount for a certain non-human animal is carried out in the same manner described below in the case of humans, and veterinarians are well accustomed to such determinations.

Further, the activity of compounds of Formula I in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula I will be set out in detail below. Again, the effective amount of a compound for the inhibition of serotonin reuptake, or for a specific therapeutic method which depends on the inhibition of reuptake, is determined in the manner described below under the heading of smoking withdrawal.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
|---|---|
| Compound of Example 20 | 30.0 |
| Starch | 305.0 |
| Magnesium stearate | 5.0 |

The above ingredients are mixed and filled into hard gelatin capsules in 340 mg quantities.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A compound of Formula I:

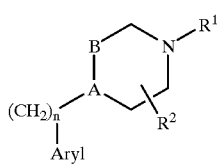

where

A—B is —C=CH— or —CHCH$_2$—;

n is 0 or 1;

R$^1$ is H or C$_1$–C$_4$ alkyl;

R$^2$ is H, methyl, or ethyl; and

Aryl is naphthyl or heteroaryl, each optionally monosubstituted with a substituent selected from the group consisting of H, halo, hydroxy, C$_1$–C$_4$ alkyl, C1–C4 alkoxy, cyano, nitro, carboxamido, and trifluoromethyl; or pharmaceutically acceptable salts or hydrates thereof, provided that when Aryl is benzofuryl, n is 1; and that when Aryl is naphthyl or benzoimidizolyl, R$^2$ must be other than hydrogen.

2. A compound claim 1 where n is 0.

3. A compound of claim 1, where A—B is —CHCH$_2$—.

4. A compound of claim 1, where Aryl is benzofur-2-yl.

5. A method for the inhibition of serotonin reuptake comprising administering to a mammal in need of such treatment an effective amount of a compound of Formula II:

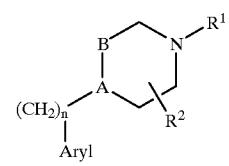

where

A—B is —C=CH— or —CHCH$_2$—;

n is 0 or 1;

R$^1$ is H or C$_1$–C$_4$ alkyl;

R$^2$ is H, methyl, or ethyl; and

Aryl is naphthyl or heteroaryl, each optionally monosubstituted with a substituent selected from the group consisting of H, halo, hydroxy, C$_1$–C$_4$ alkyl, C$_1$–C$_4$ alkoxy, cyano, nitro, carboxamido, and trifluoromethyl; or pharmaceutically acceptable salts or hydrates thereof, provided that when n is 1, A—B is —CHCH$_2$—.

6. A method of claim 5, where the mammal is a human.

7. A pharmaceutical formulation which comprises, in association with pharmaceutically acceptable carriers, diluents or excipients, a compound of Formula I:

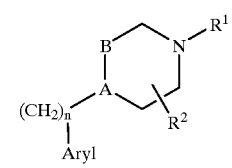

where

A—B is —C=CH— or —CHCH$_2$—;

n is 0 or 1;

R$^1$ is H or C$_1$–C$_4$ alkyl;

R$^2$ is H, methyl, or ethyl; and

Aryl is naphthyl or heteroaryl, each optionally monosubstituted with a substituent selected from the group consisting of H, halo, hydroxy, C$_1$–C$_4$ alkyl, C1–C4 alkoxy, cyano, nitro, carboxamido, and trifluoromethyl; or pharmaceutically acceptable salts or hydrates thereof, provided that when Aryl is benzofuryl, n is 1; and that when Aryl is naphthyl or benzoimidizolyl, R$^2$ must be other than hydrogen.

* * * * *